United States Patent [19]
Bandurski et al.

[11] Patent Number: 5,919,998
[45] Date of Patent: Jul. 6, 1999

[54] GENETIC CONTROL OF PLANT HORMONE LEVELS AND PLANT GROWTH

[75] Inventors: Robert S. Bandurski, East Lansing; Jedrzej Bogumil Szerszen, deceased, late of East Lansing, by Agathe J. Schulze, executrix; Krzysztof Szczyglowski, East Lansing, all of Mich.

[73] Assignee: Michigan State University Board of Trustees, East Lansing, Mich.

[21] Appl. No.: 08/466,583

[22] Filed: Jun. 6, 1995

Related U.S. Application Data

[62] Division of application No. 08/265,427, Jun. 24, 1994.

[51] Int. Cl.$^6$ .............................. A01H 5/00; C12N 15/29; C12N 15/54; C12N 15/82
[52] U.S. Cl. .......................... 800/286; 800/290; 800/298; 800/317; 800/320; 800/320.1; 800/320.2; 800/320.3; 435/69.1; 435/70.1; 435/193; 435/468; 536/23.2; 536/23.6; 536/24.5
[58] Field of Search .................................. 536/23.2, 23.6, 536/24.5; 435/69.1, 70.1, 172.3, 193, 468; 800/205, DIG. 26, 40, 55–58, 286, 290, 298, 317, 320, 320.1, 320.2, 320.3

[56] References Cited

U.S. PATENT DOCUMENTS 4,801,540  1/1989  Hiatt et al. ............................ 435/172.3

OTHER PUBLICATIONS

Ragland et al. J. Biol. Chem. 265(30):18339–18344, Oct. 1990.
Smith et al. 1988. Nature 334:724–726.
Sheehy et al. 1988. Proc. Natl. Acad. Sci. USA 85:8805–8809.
Chang et al. 1985. Mol. Cell. Biol. 5(9):2341–2348.
Szerszen et al. (1994) "Cloning of the Genes for Metabolism of Indole–3–acetic Acid" *Plant Physiol.* 105:16 Suppl. 1 May.
Szerszen et al. (1993) "A Strategy to Regulate IAA Conjunction in Transgenic Plants", *Phytopathology 83:1380* No. 12.
Yang et al. (1993) "Magnitude and Kinetics of Stem Elongation Induced by Exogenous Indole–3–Acetic Acid in Intact Light–Grown Pea Seedlings", *Plant Physiol.* 102:717–724.
Van Onckelen et al. (1985) "Tobacco Plants Transformed with the *Agrobacterium* T–DNA gene 1 Contain High Amounts of Indole–3–acetamide", *FEBS Letters 131:373–376*.
Klee et al. (1987) "The Effects of Overproduction of Two *Agrobacterium tumefaciens* T–DNA Auxin Biosynthetic Gene Products in Transgenic Petunia Plants", *Genes & Devel.* 1:86–96.
Follin et al. (1985) *Mol. Gen. Genet.* 201:178–185.
Kowalczyk and Bandurski (1991) *Biochem. J.* 279:509–514.
Leznicki and Bandurski (1988) "Enzymatic Synthesis of Indole–3–Acetyl–1–β–D–Glucose I.", *Plant Physiol.* 88:1474–1480 No. 4.
Leznicki and Bandurski (1988) "Enzymatic Synthesis of Indole–3–Acetyl–1–β–D–Glucose II.", *Plant Physiol.* 88:1481–1485 No. 4.
Michalczuk and Bandurski (1982) "Enzymic Synthesis of 1–O–indol–3–ylacetyl–β–D–glucose and Indol–3–ylacetyl–myo–inositol", *Biochem. J.* 207: 273–281.
Rayle and Cleland (1992) "The Acid Growth Theory of Auxin–Induced Cell Elongation is Alive and Well", *Plant. Physiol.* 99:1271–1274.
Sitbon, F. (1992) "Transgenic Plants Overproducing IAA—A Model System to Study Regulation of IAA Metabolism", Swedish University of Agricultural Sciences, Umea, Sweden, pp. 6–59.

*Primary Examiner*—David T. Fox
*Attorney, Agent, or Firm*—Greenlee, Winner and Sullivan, PC

[57] ABSTRACT

Plant growth and plant growth habit can be controlled without the application of exogenous plant hormones or hormone mimetics using the nucleic acid sequences and methods provided. UDP-Glucose: Indol-3-ylacetyl-glucosyl transferase (IAGlu Transferase) amino acid sequence and nucleic acid coding sequences for this enzyme, specifically exemplified for *Zea mays*, are provided. Nucleic acid constructs directing the expression of IAGlu Transferase and the expression of antisense RNA specific therefor allows the control of growth habit and plant size in transgenic plants containing such nucleic acid constructs.

21 Claims, 6 Drawing Sheets

GENETIC CONTROL OF PLANT HORMONE LEVELS AND PLANT GROWTH

This application is a divisional application of co-pending U.S. patent application Ser. No. 08/265,427, filed Jun. 24, 1994.

This invention was made, at least in part, with funding from the National Science Foundation (Grant No. IBN 92-07743). Accordingly, the United States Government may have certain rights in this invention.

FIELD OF THE INVENTION

This invention relates to the control of plant hormone levels and of plant growth at the molecular genetic level. It particularly relates to nucleotide sequences encoding UDP-glucose:indol-3-ylacetyl-glucosyl transferase, and the use of these sequences and/or subsequences thereof to regulate plant growth.

BACKGROUND OF THE INVENTION

Plant growth is affected by a variety of physical and chemical factors. Physical factors include available light, day length, moisture and temperature. Chemical factors include minerals, nitrates, hormones and cofactors.

One of the most common plant growth hormones is indole-3-acetic acid (IAA). IAA is often referred to as "auxin." IAA has been demonstrated to be directly responsible for increase in growth in plants in vivo and in vitro. Those characteristics influenced by IAA include cell elongation, internodal distance (height), leaf surface area and crop yield.

Most plant tissues contain about $10^{-8}$M free IAA. There appears to be two basic pathways for the synthesis of IAA in plants, one via tryptophan and one probably through indole. These same tissues contain about 20 times that amount of IAA in the form of ester or amide conjugates; most commonly the IAA is covalently bound to a sugar moiety. This 20:1 ratio of conjugated to free IAA is generally observed even in tissues which are known to be limited in growth rate by the amount of free IAA.

The first step in the biosynthesis of conjugates of IAA in Zea mays is catalyzed by UDP-glucose:indol-3-ylacetyl-glucosyl transferase (EC 2.4.1.121; also called IAA-Glucose Synthetase, IAGlu Synthetase, IAGlu Transferase). This enzyme has been purified, and its characteristics have been described (Kowalczyk and Bandurski (1991) *Biochem. J.* 279:509–514; Leznicki and Bandurski (1988) *Plant Physiol.* 88:1481–1485 and 88:1474–1480). The substrates for IAGlu Transferase are UDP-glucose and IAA, and the reaction product is 1-0-β-D-indol-3ylacetyl-glucose. IAA-glucose can be hydrolyzed by one of two hydrolases, depending on the isomeric form. These hydrolases effectively impart reversibility to the synthetase reaction.

IAGlu is an acyl alkyl acetal, and its energetically unfavorable synthesis is followed by an energetically favorable transacylation of IAA from IAGlu to myo-inositol to yield indol-3-ylacetyl-myo-inositol (Michalczuk and Bandurski (1982) *Biochem. J.* 207:273–281). The enzyme indol-3-ylacetylglucose-myo-inositol indol-3-ylacetyltransferase (IAInos synthetase) catalyzes this reaction (Reaction D, FIG. 1). IAInos is believed to be a transport form of IAA, and IAInos is the substrate for the synthesis of IAInos-glycosides. Thermodynamically, IAInos synthetase is believed to be the enzyme which shifts the equilibrium from free IAA to conjugated forms of IAA. Conjugates appear to serve functions other than growth promotion such as IAA transport (Nowacki and Bandurski (1980) *Plant Physiol.* 65:422), protection of IAA against peroxidative attack (Cohen and Bandurski (1978) *Planta* 139:203), storage of IAA in seeds (Bandurski et al. (1991) in *Plant Growth Substances*, C. M. Karssen (ed.), Kluwer Academic Publishing, Amsterdam, pp. 1–12) and hormonal homeostasis (Bandurski et al. (1988) in *Plant Growth Substances*, Pharis and Rood (eds.), Springer-Verlag, Berlin, pp. 341–352).

There have been attempts to improve crop yield by increasing the level of IAA in plants both by application of exogenous IAA and by increasing the synthesis of endogenous IAA. Yang et al. (1993) *Plant Physiol.* 102:717–724 report that exogenously applied IAA, via cotton wicking in contact with apical stem parts, stimulated stem elongation, particularly in dwarf plants. Application of exogenous IAA is not practical because the effect is limited in time and such application at the agricultural level would be prohibitively labor-intensive and expensive.

Attempts to increase the endogenous synthesis of IAA have involved the genetic engineering of plants to contain bacterial genes for the biosynthesis of IAA. There have been several reports that expression of the *Agrobacterium tumefaciens* IAA biosynthetic pathway genes did not result in increased plant growth (Follin et al. (1985) *Mol. Gen. Genet.* 201:178–185; van Onckelen et al. (1985) *FEBS Letters* 181:373–376). Generally transgenic plants expressing higher levels of IAA via bacterial enzymes showed phenotypic abnormalities (Klee et al. (1987) *Genes Devel.* 1:86–96; Schmulling et al. (1988) *EMBO J.* 7:2621–2629). Such transgenic plants exhibited higher than normal levels of both IAA conjugates and of free IAA, particularly when the bacterial iaaM and/or iaaH genes were linked to powerful heterologous promoters (Sitbon, F. (1992) *Transgenic Plants Overproducing IAA—A Model System to Study Regulation of IAA Metabolism*, Swedish University of Agricultural Sciences, Umea, Sweden).

SUMMARY OF THE INVENTION

It is an object of this invention to provide the nucleotide sequences encoding IAGlu Transferase and non-naturally occurring DNA molecules containing these sequences. An exemplary IAGlu Transferase coding sequence is that of *Zea mays*; as specifically exemplified herein, this sequence is presented in SEQ ID NO:1 from nucleotide 57 to nucleotide 1472. Equivalents of the exemplified nucleotide sequence are those nucleotide sequences which encode a polypeptide with the specifically exemplified amino acid sequence given in SEQ ID NO:2 and those nucleotide sequences which encode a polypeptide with equivalent enzymatic activity and which nucleotide sequences have substantial sequence identity (at least about 70%) to the exemplified sequence, i.e., can hybridize with the exemplified sequences under conditions of moderate or greater stringency as understood in the art.

It is a further object of this invention to provide for transcriptional expression of sequences complementary to the IAGlu Transferase coding sequences to reduce IAGlu Transferase gene expression in transgenic plants in order to down-regulate synthesis of the IAGlu Transferase in those plants, thus allowing for control of the proportions of free and bound IAA, thereby allowing for control of the growth habit of said plants. Conversely, transgenic plants which overexpress IAGlu Transferase are also taught herein. An iaglu coding sequence linked to either a regulated or a constitutive promoter can be introduced into plant tissue, and a transgenic plant regenerated, whereby control of the growth habit results from the relative overproduction of IAGlu Transferase in said plant. Overproduction of IAGlu synthetase results in loss of apical dominance, and a more prostrate plant than the wild-type parent plant.

BRIEF DESCRIPTION OF THE DRAWINGS

FIG. 4B illustrates pBI121 into which the iaglu cDNA has been cloned downstream of the CaMV 35S promoter in the antisense direction with respect to the direction of transcription directed by the promoter. See also Example 7.

DETAILED DESCRIPTION OF THE INVENTION

U.S. Pat. No. 5,190,931 (M. Inouye, issued Mar. 2, 1993) refers to methods for down-regulating target gene expression via expression of antisense molecules having nucleotide sequences complementary to portions of the target gene. Hybrid formation, between the antisense molecule and the target gene mRNA results in inhibition of translation of the target gene's mRNA into a functional gene product. U.S. Pat. No. 5,190,931, which is incorporated by reference herein, further teaches that the antisense of RNA specifically blocks the expression of complementary sequences, that the inhibition expression occurs very rapidly, the amount of target mRNA is reduced, and the more antisense RNA is made, the greater the inhibition of target gene product expression.

U.S. Pat. No. 4,801,540 (Hiatt et al., issued Jan. 31, 1989) refers to the tomato polygalacturonase coding sequence and antisense sequences derived therefrom useful for regulating the levels of polygalacturonase, particularly in the fruits of transgenic plants expressing those antisense sequences.

Figure 1:
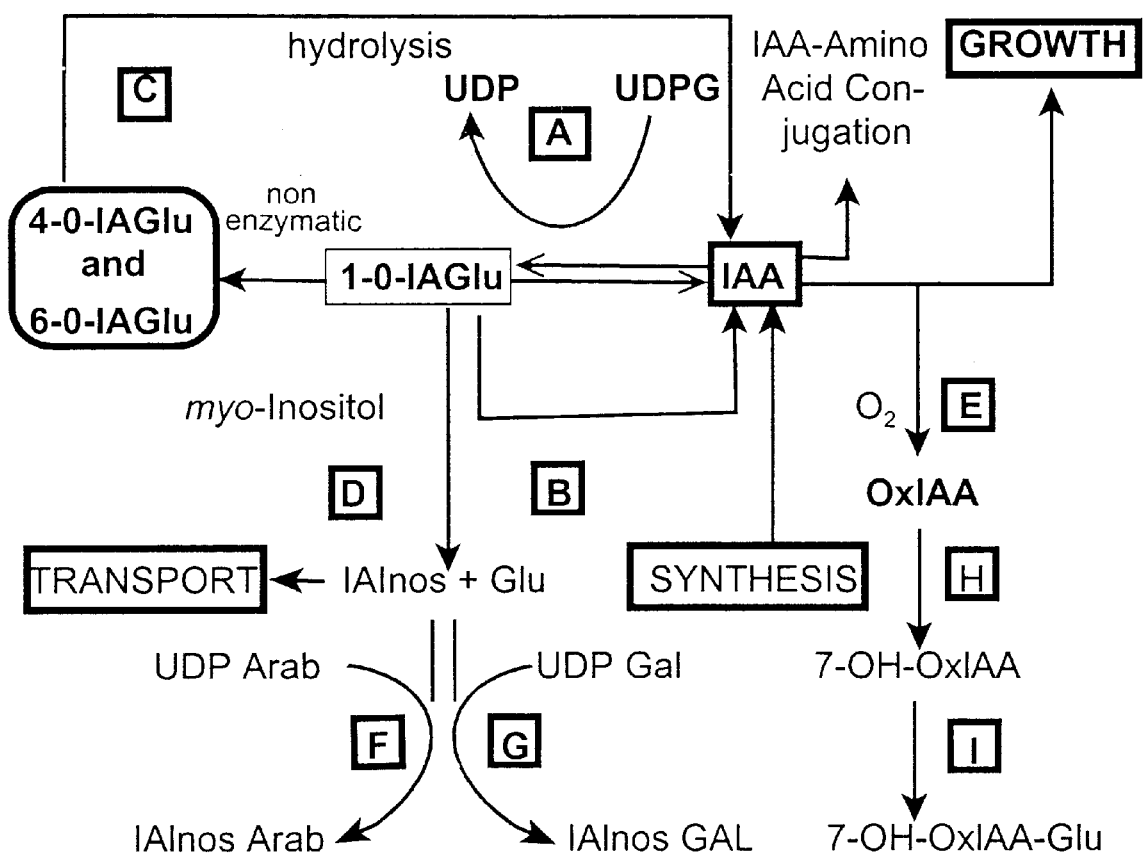
FIG. 1 illustrates metabolic reactions affecting the concentration of indole-3-acetic acid in Zea mays. Reaction A, carried out by IAGlu Transferase, is the synthesis of 1-0-IAA-Glucose (IAGlu) from IAA and UDP-glucose. Reaction B is the enzymatic hydrolysis of 1-0-IAGlu; the equilibrium is toward free IAA. Reaction C is the enzyme-catalyzed hydrolysis of 4-0-IAGlu and 6-0-IAGlu, which are produced by isomeration of 1-0-IAGlu. Reaction D is the enzyme-catalyzed transacylation of IAA from 1-0-IAGlu to myo-inositol to form the ester (IAInos), thus shifting the equilibrium towards esterified IAA. Reaction E is the oxidation of IAA to oxindole-3-acetic acid (OxIAA). Reactions F and G represent the glycolysation of IAInos, which further shifts the equilibrium towards IAA esters. Reaction H is the benzene ring hydroxylation of OxIAA to form 7-hydroxy-oxindole-3-acetic acid (7-OH-OxIAA). Reaction J is the glucosylation of 7-OH-OXIAA at the 7-hydroxyl; this reaction may target the molecule for inclusion into a vacuole and further catabolism. Under certain conditions young maize seedlings do not synthesize IAA de novo; the synthesis of IAA is not included in this metabolic scheme.

In all plants studied, indole-3-acetic acid (IAA) functions as a growth regulator. FIG. 1 illustrates the reactions involving IAA and its conjugates in plants. Generally, there is a 20:1 ratio of conjugate-bound IAA to free IAA, and it has been suggested that it is the free IAA concentration which is limiting to plant growth. The IAA-conjugates do not appear to have the physiological effects attributed to IAA, i.e., the pool of IAA-conjugates appear to be ineffective at stimulating plant growth (Cohen and Bandurski (1982) Annu. Rev. Plant Physiol. 33:403). The first reaction in producing IAA conjugates is catalyzed by IAGlu Transferase. Thus, the ability to control, i.e., limit, the expression of IAGlu Transferase allows the control of free IAA levels in a plant by shifting the equilibrium in favor of free IAA, thereby effecting faster plant growth rates and greater crop yields.

The following definitions of terms used herein are provided for added clarity to the skilled artisan reader.

IAGlu Transferase means UDP-glucose:indol-3-ylacetyl-glucosyl transferase (EC 2.4.1.121; also called IAA-Glucose Synthetase, IAGlu Synthetase, IAGlu Transferase). It catalyzes the reaction between UDP-glucose and indol-3-ylacetic acid to yield 1-0-β-D-indol-3-ylacetyl-glucose. Within the scope of the present invention are truncated forms and variants of IAGlu Transferase which retain the enzymatic activity of the naturally occurring enzyme. The gene and cDNA encoding this enzyme are termed iaglu.

A non-naturally occurring DNA molecule is one which does not occur in nature; i.e., it is produced either by natural processes using methods known to the art, but is directed by man to produce a desired result or it has been artificially produced from parts derived from heterologous sources, which parts may be naturally occurring or chemically synthesized molecules or portions thereof, and wherein those parts have been joined by ligation or other means known to the art.

A transgenic plant is one which has been genetically modified to contain and express heterologous DNA. As specifically exemplified herein, a transgenic plant is genetically modified to contain and express an iaglu coding sequence operably linked to transcriptional control sequences by which it is not normally regulated or to contain and express an iaglu DNA sequence or portion thereof oriented opposite in direction to the coding sequence with the transcriptional control sequences directing the synthesis of an RNA complementary to all or a portion of the iaglu mRNA. As used herein, a transgenic plant also refers to progeny of the initial transgenic plant which progeny carry and are capable of expressing the heterologous iaglu coding sequence or iaglu antisense construct. Seeds containing transgenic embryo are encompassed within this definition.

An antisense nucleic acid molecule is one which is complementary in sequence, according to the well-known rules for nucleotide base-pairing, and capable of binding or hybridizing to a target nucleic acid molecule, either over a portion or over its whole length. In order to effectively inhibit the expression of a target mRNA sequence (in the present case, the mRNA encoding IAGlu synthetase), the antisense molecule is at least about 10 nucleotides in length, more generally at least about 15 nucleotides, and up to and including, the entire coding sequence and/or the entire cDNA sequence of SEQ ID NO:1. When the antisense molecule is RNA, then it is termed an antisense RNA. One cellular iaglu target for the antisense nucleic acid, e.g., antisense RNA, can be the iaglu mRNA so that translation of the iaglu mRNA is inhibition. Additionally, inhibition of IAGlu Transferase can be via DNA:DNA:RNA triplex formation, which inhibits transcriptional expression of iaglu mRNA.

When enhanced production of IAGlu Transferase is desired, the IAGlu Transferase coding sequence is operably linked in the sense orientation to a suitable promoter, in the same orientation as the promoter, so that a sense (i.e., functional for translational expression) mRNA is produced. A transcription termination signal functional in a plant cell can be placed downstream of the coding sequence, and a selectable marker which can be expressed in a plant, can be covalently linked to the IAGlu Transferase expression unit so that after this DNA molecule is introduced into a plant cell or tissue, its presence can be selected and plant cells or tissue not so transformed will be killed or prevented from growing.

Where inhibition of IAGlu Transferase expression is desired in a plant, then either a portion or all of the IAGlu Transferase coding sequence or cDNA sequence can be operably linked to a promoter functional in plant cells, but with the orientation of the IAGlu Transferase coding sequence opposite to that of the promoter (i.e., in the antisense orientation) so that the transcribed RNA made is complementary in sequence to the mRNA encoding IAGlu Transferase. In addition, there may be a transcriptional termination signal downstream of the nucleotides directing synthesis of the antisense RNA.

The present inventors have isolated a cDNA sequence encoding IAGlu Transferase from *Zea mays* (maize). This sequence is given in SEQ ID NO:1, and the deduced amino acid sequence encoded by the open reading frame of 1413 nucleotides is given in SEQ ID NO:1. The open reading frame extends from an ATG beginning at nucleotide 57 through the stop codon ending at nucleotide 1472 in SEQ ID NO: 1. The open reading frame was rich in G and C nucleotides (36.7% G and 33.0% C), and therefore, it was found to be useful to incorporate deaza-GTP in the sequencing reactions to reduce band compression. The calculated molecular weight (MW) of the encoded protein is 49.71 kDa and the estimated pI is 5.69. These values are in good agreement with the MW and pI values obtained previously by electrophoresis of purified IAGlu synthetase: 51.0 kDa (Kowalczyk and Bandurski (1991) supra), and 5.5 (Leznicki et al. (1988) *Plant Physiol.* 88:1474), respectively. Hydropathy analysis was carried out using the MacVector computer program, release 3.5 (International Biotechnologies, Inc., New Haven, Conn.) and a window size of 7; it was based on the Kyte-Doolittle method (Kyte and Doolittle (1982) *J. Mol. Biol.* 157:105). This analysis (see FIG. 2) revealed the presence of four major hydrophilic regions (amino acid residues 1 to 279, 293 to 299, 399 to 406, and 435 to 444 of SEQ ID NO:2) of the encoded protein. Further computer analyses of the deduced amino acid sequence revealed a potential glycosylation site (N-X-S/T) at amino acid 363 (in SEQ ID NO:2) and three potential protein kinase C phosphorylation sites (S/T-X-R/K) have been identified at amino acid residues 37, 453, and 469 (in SEQ ID NO:2).

The catalytic activity of the protein synthesized by *E. coli* cells containing the cDNA insert from clone #3, cloned into the EcoRI site of pBluescript KS⁻, was examined as described in Example 5 herein. Bacteria containing pBluescript KS⁻ without an insert and bacteria containing a shorter antibody-positive cDNA (clone #2, 1050 bp) were used as negative controls. Both controls were totally inactive in synthesizing labeled IAGlu from labeled IAA and UDP-glucose. Extracts from cells expressing the cDNA from clone #3 synthesized $^{13}C_6$-labeled IAGlu yielding $(M)^+$= 343.143 and $(M+Na)^+$=366.126 when incubated with $^{13}C_6$-labeled IAA and UDP-Glucose, as determined by Fast Atom Bombardment mass spectrometry. These are the masses calculated for $^{13}C_6C_{10}H_{19}O_7N$ and $^{13}C_6C_{10}H_{19}O_7NNa$ and this analysis proves the identity of the heavy atom labeled IAGlu. Authentic unlabeled IAGlu yielded $(M)^+$ of 337.118 and $(M+Na)^+$ of 360.113. The activity of the cloned iaglu gene product in *E. coli* suggests that if in plants the potential glycosylation sites are glycosylated, such glycosylation is not required for enzymatic activity, as bacterial hosts are not believed to effect glycosylation of eukaryotic gene products.

A preparation of maize IAGlu synthetase, purified as described by Kowalczyk and Bandurski (1991) supra, was further purified by chromatography on a $C_{18}$ 1 mm×250 mm HPLC column using 0.1% trifluoroacetic acid (TFA) as solvent and a gradient of 90% (v/v) acetonitrile-water containing 0.85% TFA. Some protein degradation occurred, but the single major peak was collected for N-terminal sequencing. The amino acid sequence obtained from the N-terminus of the protein was MAPXVLVVPFPGQGXMNP (SEQ ID NO:3), where "X" is an amino acid not conclusively identified. This corresponds exactly with the N terminal amino acid sequence deduced from the nucleotide sequence of the isolated clone (see SEQ ID NO:1 and 2). The two amino acids not identified in the N-terminal sequencing experiment were shown to be histidine residues by nucleotide sequence analysis.

A computer search for alignment of amino acid residues of the iaglu coding sequence with known amino acid sequences showed localized regions with significant sequence identity with other known UDP-Glucose- and UDP-Glucuronic-transferase proteins (Table 1). Alignment of portions of the predicted amino acid sequence of the iaqlu gene from *Zea mays* with (Table 1A) human HlugP4 gene product (human liver phenol/bilirubin UDP-glucuronosyltranferase) shows a 68% sequence similarity (44% identity) over a stretch of 56 residues; with a *Zea mays* bzl gene product (Bz-McC allele) (UDP-glucose:flavenol 3-0-glucosyltransferase) 59% similarity (49% identity) over 131 residues; and Table 1B with the *Oryctolaqus cuniculus* UGT2B13 gene product (rabbit liver p-nitrophenol UDP-glucuronyltransferase) 48% similarity (59% identity) over 52 residues; and with the *Rattus norvegicus* rluq23 gene product (rat liver androsterone UDP-glucuronyl transferase) 55% similarity (44% identity) over 58 residues.

TABLE 1

Alignment of Portions of the Maize IAGlu Transferase
Amino Acid Sequence with UDP-glycosylating Enzymes[a]

A

```
HlugP4[b]                                                                            349 ILV
                                                                                         ::|
IAGlu[c]     268 CTKWLDTKPDRSVAYVSFGSLASLGNAQKEELARGLLAAGKPFLWVVRASDEHQVPRYLLAEATATGAAMVV
                 |  ||  :|  |  ||||||||::|      :   ||| ||  :| ||||  :|         :|   |   |   ||: :||
bzl[d]       103 CLAWLGRQPARGVAYVSFGTVACPRPDELRELAAGLEDSGAPFLWSLREDSWPHLPPGFLDRAAGTGSGLVV HlugP4       352 KWLPQNDLLGHPMTRAFITHAGSHGVYESICNGVPMVMMPLFGDQMDNAKRME
                 |  ||  |:| ||      |:|| |  :       |::    |||||  |  |: ||    ||: :|
IAGlu        340 PWCPQLDVLAHPAVGCFVTHCGWNSTLEALSFGVPMVAMALWTDQPTNARNVELAWGAG
                 ||  ||:  ||   ||:||   ||||  ||  |  ||  ||  ||||          :  ||   |||:|      ||  |
bzl          175 PWAPQVAVLRHPSVGAFVTHAGWASVLEGLSSGVPMACRPFFGDQRMNARSVAHVWGFG
```

B

```
UGT2B13[e]   329             WIPQNDLLGHPKTRAFITHGGTNGLYEAIYHGVPMVGIPLFGDQPDNIARVK
                             |  ||  |:|  ||         |:|| |   |       ||:    ||||| |  :|: |||   |:::|:
IAGlu[f]     330 ATATGAAMVVPWCPQLDVLAHPAVGCFVTHCGWNSTLEALSFGVPMVAMALWTDQPTNARNVE
                 ||            |    |  || |:|  ||        ||||  |  |      ||:    |:||:  :   |:  ||| |
rlug23[g]    316 ATLGPITRVYKWLPQNDILGHPKTKAFVTHGGANGLYEAIYHGIPMIGIPLFGDQPDN
```

[a]Bars indicate identical amino acids; dots indicate amino acids with similar properties.
[b]Human (HlugP4) (human liver phenol/bilirubin UDP-glucuronosyltransferase) amino acid sequence for residues 349–404 (SEQ ID NO: 4) (Wooster et al. (1991) Biochem. J. 278:465).
[c]Maize IAGlu Transferase amino acid sequence for residues 268–398 (SEQ ID NO: 5).
[d]Maize BZL (McC allele) (UDP-glucose:flavenol 3-0-glucosyltransferase) amino acid sequence for residues 103–233 (SEQ ID NO: 6) (Furtek et al. (1988) Plant Molec.Biol. 11:473).
[e]*Oryctolagus cuniculus* (UGT2B13) (rabbit liver p-nitrophenol UDP-glucuronyltransferase) amino acid sequence for residues 329–380 (SEQ ID NO: 7) (Tukey et al. (1993) J.Biochem 268:15260).
[f]Maize IAGlu Transferase (IAGlu) amino acid sequence for residues 330–392 (SEQ ID NO: 8).
[g]*Rattus norvegicus* rlug23 gene product amino acid sequence (rat liver androsterone UDP-glucuronyl transferase) for residues 316–373 (SEQ ID NO: 9) (Jackson and Burchell (1986) Nucl. Acids Res. 14:779).

Figure 3:
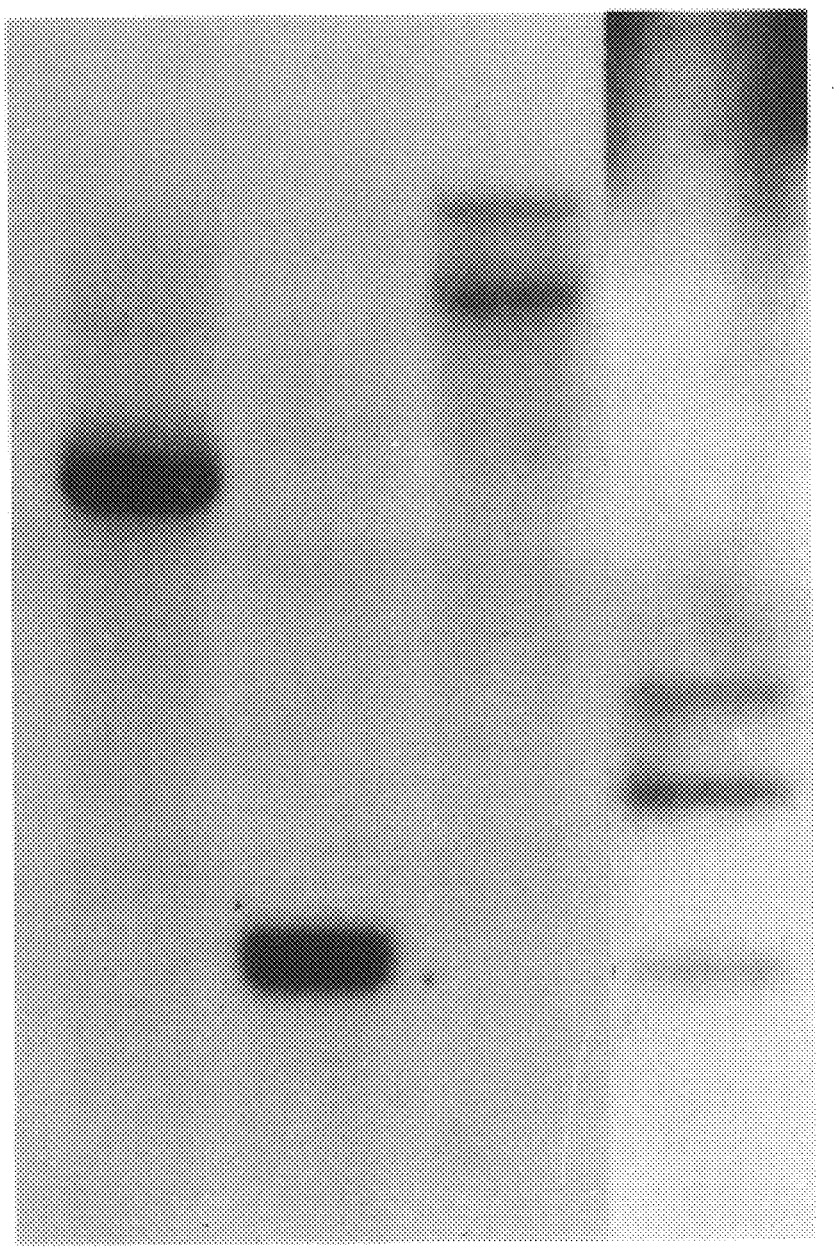
FIG. 3 is an autoradiograph from a Southern hybridization experiment using [$^{32}$P]-labeled cDNA encoding IAGlu synthetase from maize as probe. Lanes 1, 2 and 3 contain Zea mays total DNA digested with EcoRI, HindIII and BamHI, respectively, hybridized under conditions of high stringency to the maize iaglu cDNA probe. Lane 4 contains Arabidopsis thaliana DNA, digested with EcoRI and hybridized under conditions of moderate stringency to the maize iaglu cDNA probe. The positions of molecular size standards are shown at right.

Organization of the iaglu gene in the *Zea mays* genome was studied using radiolabeled iaglu cDNA sequence (SEQ ID NO: 1; 1731 bp) as a probe in Southern hybridizations (FIG. 3). Under high stringency conditions, a single EcoRI or HindIII fragment and two BamHI fragments hybridized indicating that IAGlu Transferase is probably encoded by a single or low copy number gene in the maize genome. There does not, however, appear to be a BamHI site in the iaglu cDNA.

In addition, genomic DNA (as EcoRI digests) from a variety of plant species including *Arabidopsis thaliana*; *Nicotiana tabacum*, tobacco; *Beta vulgaris*, sugar beet; *Lycopersicon esculentum*, tomato; *Glycine max*, soybean; *Brassica oleracea* var. botrytis, cauliflower; *Sorghum bicolor*, sorghum; *Triticum vulgare*, wheat; the legume *Lotus japonicus*; and *Lemna gibba*, duckweed were analyzed for significant nucleotide sequence homology to maize iaglu cDNA sequences. Genomic DNA from the bryophyte Marchantia, the fern *Osmunda claytoniana*; the moss *Selaginella kraussiana*, the pteridophyte Psilotum (liverwort) and Equisetum (horsetail) were also analyzed. In all cases, under hybridization conditions of moderate stringency, multiple hybridizing bands (major and several minor) were observed. Without wishing to be bound by any particular theory, the inventors postulate that this reflects hybridization of the *Z. mays* iaqlu cDNA probe to the equivalent iaqlu genes of these plants species, as well as to other genes encoding UDP-glucose or UDP-glucuronic acid binding proteins. An example of Southern hybridization analysis for *Z. mays* and *A. thaliana* is shown in FIG. 3. Three hybridizing bands were observed using moderately stringent conditions. However, under high stringency conditions only a single 3 kb hybridizing band was detected. The same single band was detected under moderately stringent conditions when the 5'-region of the iaglu cDNA (nucleotides 1 through 598 of SEQ ID NO: 1, lacking the putative UDPG-binding site) was used as a probe, suggesting that this 3 kb band contains the *A. thaliana* iaglu gene.

Figure 2:
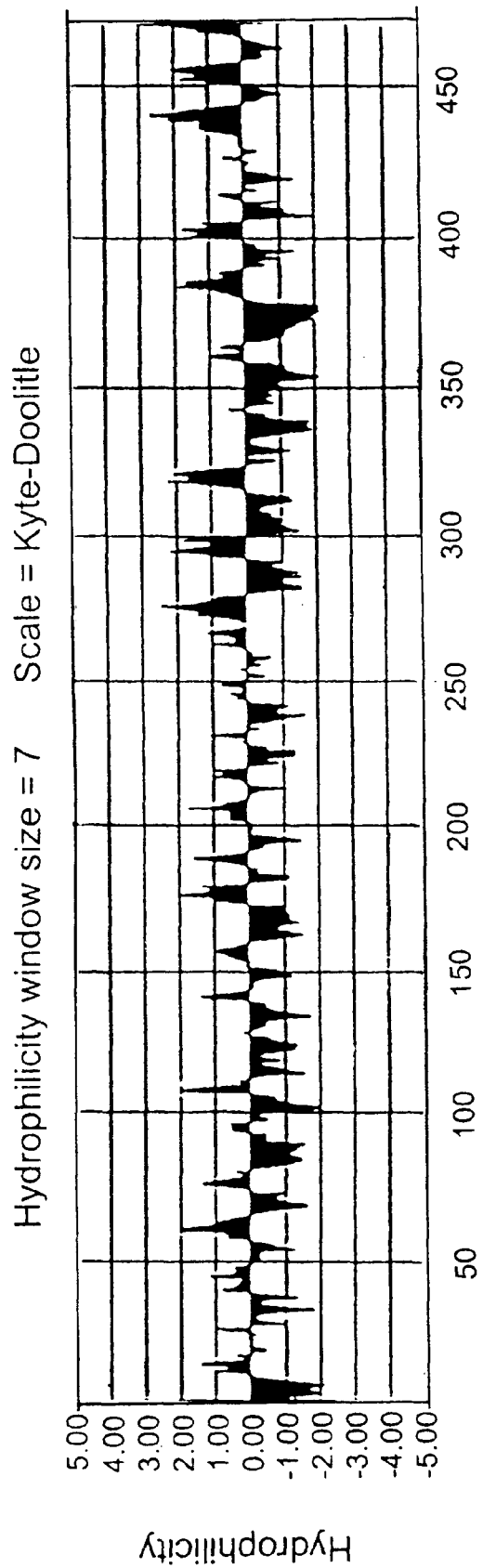
FIG. 2 is the hydropathy plot of the deduced amino acid sequence (see also SEQ ID NO:2) of the maize iaglu gene product. Negative values indicate hydrophobic residues and positive values indicate hydrophilic regions of the protein.

These experiments indicated that there is a detectable amino acid sequence identity of a specific segment of the iaglu gene with conserved domains of certain other known enzymes which use UDP-Glucose and/or UDP-Glucuronic acid as substrates. Because these enzymes catalyze the transfer of either glucose or glucuronic acid to their specific acceptors, the conserved amino acids probably represent those necessary to bind UDP. This suggests that the UDP-Glucose binding site is located within the region of amino acids 268 through 393 of the maize IAGlu Transferase (see SEQ ID NO:2). This region corresponds to the most hydrophobic portion of the predicted amino acid sequence of the iaglu gene product as shown in FIG. 2.

The hybridization results demonstrate that plant species other than *Zea mays* have IAGlu Transferase genes with significant degrees of nucleotide sequence homology; i.e., DNA:DNA hybridization under conditions of moderate to high stringency with the *Zea mays* iaglu probe allows the identification of the corresponding gene from other plant species. A discussion of hybridization conditions can be found for example, in Hames and Higgins (1985) *Nucleic Acid Hybridization*, IRL Press, Oxford, U.K. Generally sequences which have at least about 70% nucleotide sequence homology can be identified by hybridization under conditions of moderate stringency. Under such conditions, it is generally preferred that a probe of at least 100 bases be used. Most preferably, in the present case, the probe will be derived from the portion of the iaglu cDNA sequence 5' of the region encoding the putative UDP-binding region. The UDP binding region of the maize IAGlu Transferase is encoded beginning at about nucleotide 858 in SEQ ID NO:1. Preferably, a probe corresponding to the portion of the maize iaglu coding sequence 5' to the UDP-binding region, which begins at about nucleotide 858 in SEQ ID NO: 1, is used so that DNA encoding other UDP-binding enzymes is not hybridized.

Labels for hybridization probes can include, but are not limited to, radioactive groups, fluorescent groups, ligands such as biotin to which specific binding partners (which are in turn labeled) bind. It is the label which allows detection of the hybridization probe to the target nucleic acid molecule.

It is understood that nucleic acid sequences other than that of SEQ ID NO:1, from nucleotide 57 through nucleotide 1469, will function as coding sequences synonymous with the exemplified coding sequence. Nucleic acid sequences are synonymous if the amino acid sequences encoded by those nucleic acid sequences are the same. The degeneracy of the genetic code is well known to the art; i.e., for many amino acids, there is more than one nucleotide triplet which serves as the codon for the amino acid. It is also well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

IAGlu Transferase genes can be found in all plants, including but not limited to those which have been demonstrated to contain sequences of significant homology, as disclosed herein. Such iaglu sequences can be identified by nucleic acid hybridization experiments or when cloned in expression vectors, by cross reaction to maize IAGlu Transferase-specific antibody, or any other means known to the art, including the use of PCR technology carried out using oligonucleotides corresponding to portions of SEQ ID NO:1, preferably 5' of the region encoding the UDP-binding region of IAGlu Transferase. Such antibody can be prepared after immunizing an experimental animal with purified IAGlu Transferase or using a carrier protein-peptide conjugate, where the amino acid sequence of the peptide is taken from a hydrophilic portion of the maize IAGlu Transferase amino acid sequence (see FIG. 2, SEQ ID NO:2).

Alternately, a cDNA library (in an expression vector) can be screened with IAGlu Transferase-specific antibody as described herein, or IAGlu Transferase peptide-specific antibody can be prepared using peptide sequence(s) from hydrophilic regions of the IAGlu Transferase protein (see FIG. 2 and SEQ ID NO:2) and technology well known in the art.

An IAGlu Synthetase coding sequence (cDNA or genomic) can be operably linked to any transcriptional control sequence functional in plants as understood by the skilled artisan. Constitutive promoters include those from *A. tumefaciens* T-DNA genes such as nos, ocs and mas and plant virus genes such as the Cauliflower Mosaic Virus 35S and 19S genes. Any art-known regulatory sequences, promoter and/or promoter-associated sequences which direct gene expression in the desired infected or uninfected host or infected or uninfected host cell may be used to control transcription and translation of a nucleotide sequence encoding IAGlu Transferase. It will be understood that the goals of a skilled artisan will determine the choice of particular regulatory sequences or promoters.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (see Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraly (1989) *Sci.* 244:1293; Leemans (1993) *Bio/Technol.* 11:522; Beck et al. (1993) *Bio/Technol.* 11:1524; Koziel et al. (1993) *Bio/Technol.* 11:194; Vasil et al. (1993) *Bio/Technol.* 11:1533). Techniques are well known to the art for the introduction of DNA into monocots as well as dicots, as are the techniques for culturing such plant tissues and regenerating those tissues. Monocots which have been successfully transformed and regenerated include wheat, corn, rye, rice and asparagus. For efficient regeneration of transgenic plants, it is desired that the plant tissue used in the transformation possess a high capacity to produce shoots. For example, tobacco leaf discs and aspen stem sections have good regeneration capacity (Sitbon, F. (1992) supra).

Techniques for introducing and selecting for the presence of heterologous DNA in plant tissue are well known. For example, *A. tumefaciens*-mediated DNA transfer into plant tissue, followed by selection and growth in vitro and subsequent regeneration of the transformed plant tissue to a plant is well known for a variety of plants.

Other techniques for genetically engineering plant tissue to contain an expression cassette comprising a suitable promoter fused to the iaglu coding sequence and containing a transcription termination region are to be integrated into the plant cell genome by electroporation, cocultivation, microinjection, particle bombardment and other techniques known to the art. The expression cassette further contains a marker allowing selection of the expression cassette in the plant cell, e.g., genes carrying resistance to an antibiotic such as kanamycin, hygromycin, gentamicin, or bleomicin. The marker allows for selection of successfully transformed plant cells growing in the medium containing certain antibiotic because they will carry the expression cassette with resistance gene to the antibiotic.

The IAGlu transferase coding sequence disclosed herein was operably linked to the strong constitutive 35S promoter of cauliflower mosaic virus (CaMV) to produce a 35S-iaglu chimeric construct, inserted into an Agrobacterium binary vector and transferred into tobacco tissue. Transgenic tobacco plants carrying the chimeric iaglu construct were regenerated, and their growth was characterized. The young seedlings of these plants appeared to have lost the characteristic apical dominance of wild-type tobacco plants, the stem internodes were shortened to almost zero length, and there were many leafy side shoots.

Overexpression of the iaglu coding sequence in a transgenic plant affects the control of apical dominance and/or growth habit in that plant by decreasing the pool of free IAA and increasing the pool of IAA-conjugates. Apical dominance is inhibited when IAGlu Synthetase is over-expressed. Such transgenic plants display lower growth rate, multiple branching, and shoot growth which is oriented more horizontally than vertically.

This approach can be used, for example, to produce multibranched and short-trunked fruit trees for use in modern orchards, where such trees allow for easy pesticide application, harvesting, and pruning. This approach for the control of multiple branching and apical dominance can also be used for ornamental plants, for example to produce novel ground covers, and hedge- or fence-forming plants. In case of the soybean (and other plants forming fruit in the crotch of a branch), multibranching leads to an increased number of pods (fruits).

By contrast, the iaglu sequence or portions thereof, preferably those portions which are unique to iaglu can be used to generate antisense RNAs which inhibit the synthesis of IAGlu Transferase in a transgenic plant. Inhibition of IAGlu Transferase gene expression has the effect of increasing the pool of free IAA and decreasing the proportion of the total IAA pool present in bound form. Increasing the free IAA levels in a plant has the effect of increasing cell size, stem elongation and fruit development. Manipulating the expression of antisense RNA effective for the inhibition of IAGlu Transferase expression allows the skilled artisan to increase the rate of growth of entire transgenic plants or particular plant parts, if in the latter case, tissue-specific promoters are fused to the said gene (or portion thereof) oriented in the antisense configuration. This approach enables the production of large leaves in leafy crops like tobacco, lettuce, spinach, when a promoter specific for expression in leaves is used. Large pomme and stone fruits can be likewise produced, because cell size in determined by IAA, with the choice of the appropriate promoter.

In lumber trees, growth of cambium can lead to increased wood production in trees when antisense iaglu sequences are expressed via strong promoters, for example, the CaMV 35S promoter.

Faster growth of the iaglu antisense-expressing transgenic plant, for example when a constitutive promoter such as the CaMv 35S or 19S promoter drives the expression of iaglu antisense sequences, can result in plant protection against certain plant pathogens, i.e., by the phenomenon known as "disease escape." For example, fast growth of sorghum seedlings of 0–12 days of age significantly decreases the chance of infection of the seedlings' roots by germinating oospores of *Peronosclerospora sorghi*, the casual agent of sorghum downy mildew, a devastating disease of sorghum.

Constitutive promoters which function to initiate gene expression in a wide range of plants include Ti-plasmid promoters (the octopine synthetase promoter, the nopaline synthetase promoter, the mannopine synthetase promoter), the CaMV 35S and 19S promoters (from cauliflower mosaic virus), the ORF7 promoter from open reading frame of the T-DNA, among others. These promoters and their sequences are well known to the art.

Regulated promoters functional in plants include tissue-specific promoters including, but not limited to, those of the phaseolin gene (specific for developing seed), ribulose-1, 3-biphosphate carboxylase small subunit C gene, which is most abundantly expressed in leaf and stem tissues, and cab gene, which is also most abundantly expressed in leaf tissue.

Kuhlemeier et al. (1987) *Annu. Rev. Plant Physiol.* 38: 221, and references cited therein, discusses various plant gene promoters and other promoters functional in plant cells.

Elevation of free endogenous IAA levels by genetic engineering means has the advantage that the requirement for exogenous application of IAA or other auxin-simulating chemicals, such as 2, 4-D (2, 4-dichlorophenoxyacetic acid), is obviated. Genetic control of IAA levels, i.e., a plant via iaglu antisense expression, provides a means for killing field cover plants after they fulfilled their role of protecting the main fall-sown crops against such unfavorable environmental conditions as cold winds during lack of snow cover. A cover plant (preferably a legume plant) can contain an antisense construct with a promoter activated by the environmental conditions typical of the time when the cover plant is no longer needed, e.g., by warm temperature, lengthening photoperiod, or simply by application of a chemical which will activate cover crop promoter and will not be harmful to the main crop. The cover plants can be killed or inhibited in growth by expression of multiple copies of the iaglu antisense gene and the resultant overproduction of IAA at very high levels, which is known to be toxic to plants.

Inducible promoters of phytochrome (phy) genes include the following: light-triggered: e.g., the oat phyA3 promoter can be switched off/on by red/far red light (Bruce et al. (1989) *Proc. Natl. Acad. Sci. USA* 86:9692; Bruce and Quail (1990) *The Plant Cell* 2:1081–1089). Promoters activated by warm temperature can be promoters of certain heat shock protein genes (Vierling, E. (1991) *Annu. Rev. Plant Physiology Plant Mol. Biol.* 42:579–620).

Promoters activated by low temperature include that of cold-regulated genes (cor) from *Arabidopsis thaliana*, e.g., cor15a or cor15b genes (Wilhelm and Thomashow (1993) *Plant Molecular Biology* 23:1073–1077). cor15b, an apparent homologue of cor15a, is strongly responsive to cold and ABA, but not drought. Other cold-regulated gene promoters from *A. thaliana* include kin1, kin2, lti78, cor47, cor78 and rab18. (See, e.g., Horvath et al. (1993) *Plant Physiol.* 103:1047–1053).

The antisense expression of iaglu sequence also allows a means to induce flowering at a controlled time in plants specifically requiring a long or a short photoperiod. Flowering response in these plants is under hormonal control, i.e., the production of ethylene, which promotes flowering (and fruit ripening), depends on the production of IAA. Increased levels of IAA by the antisense method described herein with the use of inducible promoters from homeotic genes from flowering plants can lead to higher levels of ethylene, and thus, to the induction of flowering and/or fruit ripening.

The following examples, provided for illustrative purposes, are not intended to limit the scope of the invention. The examples use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y.; R. Wu (ed.) (1993) *Methods in Enzymology* 218; Wu et al. (eds.) Methods in Enzymology 100, 101; Glover (ed.) (1985) *DNA Cloning*, Vols. I and II, IRL Press, Oxford, UK; and Hames and Higgins (eds.)

(1985) *Nucleic Acid Hybridization*, IRL Press, Oxford, UK. References related to the manipulation and transformation of plant tissue include Kung and Arntzen (eds.) (1989) *Plant Biotechnology*, Butterworths, Stoneham, Mass.; R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) *Methods for Plant Molecular Biology*, Academic Press, San Diego, Calif.; and various volumes of *Plant Molecular Biology Manual*, Kluwer Academic Publisher, Dordrecht. I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 19:12; Davey et al. (1989) *Plant Mol. Biol.* 13:273; Walden and Schell (1990) *Eur. J. Biochem.* 192:563; Joersbo and Brunstedt (1991) *Physiol. Plant.* 81:256 and references cited in those references. Abbreviations and nomenclature, where employed, are deemed standard in the field and are commonly used in professional journals such as those cited herein. All references cited in the present application are expressly incorporated by reference herein.

EXAMPLES

Example 1
IAGlu Transferase—specific Antibodies

Rabbit polyclonal antibodies specific for maize IAGlu synthetase were prepared by two subcutaneous injections of the protein purified as described by Kowalczyk and Bandurski (1991) supra.

The anti-IAGlu synthetase polyclonal antibodies showed cross reaction with *Escherichia coli* proteins during initial screening of the cDNA library, perhaps due to the use of Freund's adjuvant during immunization. The IAGlu antibodies were purified by affinity chromatography on cyanogen-bromide-activated Sepharose 4B with coupled *E. coli* XL-1 Blue proteins as described [Harlow and Lane (1988) *Antibodies: A Laboratory Manual* (Cold Spring Harbor Laboratory Press, Cold Spring Harbor, N.Y.)]. *E. coli* XL-1 Blue has the genotype supE hsdRlac⁻F' proAB lacI$^q$ lacZ$\Delta$M15 and is described in Bullock et al. (1987) *BioTechniques* 5:376. It is preferable in the antibody purification step to use the same strain as is used as the host strain for the expression library.

Example 2
Cloning and Identification of cDNA Encoding IAGlu Transferase

A cDNA expression library, obtained from B. A. Larkins and J. E. Habben, University of Arizona, Tucson, Ariz., was prepared from poly(A)$^+$ RNA extracted from W64A$^+$ corn endosperm tissue collected 18 days after pollination. The library was constructed in a Lambda ZAP II vector (Stratagene, La Jolla, Calif.) (Short et al. (1988) *Nucleic Acids Res.* 16:758) using standard techniques. After amplification, the library contained 4.2×10$^8$ plaque forming units (pfu).

This expression library was then screened using the purified, IAGlu synthetase-specific antibody preparation described above. Eight positive clones (named #1 through #8) were identified from 1.5×10$^6$ plaques propagated on *E. coli* XL1-Blue. The β-galactosidase fusion proteins were induced by growth on medium containing isopropyl-B-D-thio-galactopyranoside. The clones positive for IAGlu Transferase-specific antibody binding were identified using reaction with alkaline phosphatase-conjugated second antibody (specific for rabbit IgG) and chromogenic insoluble alkaline phosphatase reaction product (Sambrook et al. (1989) supra).

The cDNA inserts from clones #1–8 were excised with R 408 helper phage and recircularized to generate subclones in the pBluescript SK⁻phagemid vector (Stratagene, La Jolla, Calif.) [Russel et al. (1986) *Gene* 45:333]. Both strands of the largest cDNA insert (clone #3, 1731 bp) were sequenced.

Example 3
cDNA Sequencing and Sequence Analysis

Sequence of nucleotides was determined by the chain-termination reactions using Sequenase, Version 2.0 (United States Biochemical Corp., Cleveland, Ohio) and synthetic oligonucleotide primers. Compression of bands was eliminated by use of 7-deaza dGTP. The strategy for sequencing the IAGlu Transferase cDNA entailed subcloning the following fragments of clone #3 in pK18: Eco RI-Sac I, Sac I-Sac I, Rsa I-Rsa I and Rsa I-Eco RI.

The nucleotide sequence of the cDNA insert (clone #3) and the deduced amino acid sequence were analyzed using the MacVector computer program, Release 3.5 (International Biotechnologies, Inc., New Haven, Conn.). Hydropathy analysis was based on the Kyte-Doolittle method (Kyte and Doolittle (1982) *J. Mol. Biol.* 157:105), and it was performed with a window size of 7 and using the same computer program. Computation of amino sequence identities was performed by the BLAST Network Service (National Center for Biotechnology Information, Bethesda, Md.).

Example 4
Southern Hybridization Experiments

To address the apparent number of copies per genome of the gene encoding IAGlu Transferase, and to determine whether other plant species had significantly homologous sequences, Southern hybridization experiments were carried out. Maize DNA samples (10 μg each) were digested in parallel with EcoRI, HindIII and BamHI. *A. thaliana* genomic DNA (6 μg) was digested with EcoRI.

The digested genomic DNAs were separated by agarose gel electrophoresis (0.8% agarose), and then transferred to a Hybond-N$^+$ membrane (Amersham Corp., Arlington Heights, Ill.).

cDNA insert #3 (SEQ ID NO:1) was radiolabeled using deoxyadenosine 5'-[α-$^{32}$ P] triphosphate in a random priming reaction. Hybridization was carried out essentially as described in Sambrook et al. (1989) supra. High stringency conditions were used for maize DNA (hybridization in 2× SSC, at 65° C.; last wash using 0.3× SSC, at 65° C.), and moderate stringency conditions (hybridization in 4× SSC, at 65° C.; last wash in 1× SSC, at 65° C.) were used for the *A. thaliana* genomic DNA.

Example 5
Enzymatic Activity of Recombinant IAGlu Transferase

The recombinant (putative) IAGlu Transferase was tested for enzymatic activity. The full length cDNA (SEQ ID NO:1) was ligated into pBluescript SK⁻ (Stratagene, La Jolla, Calif.) and transformed into *E. coli*. Negative controls were isogenic *E. coli* carrying the pBluescript KS⁻ without an insert or the same vector carrying a shorter, antibody-positive cDNA insert of 1050 bp. Bacterial cells were grown to early logarithmic growth phase in 200 ml of LB medium containing ampicillin. After the cells were collected by centrifugation, the cell pellet was suspended in 5 ml grinding buffer (25 mM Tris-HCl (pH 7.6), 2 mM EDTA, 2 mM dithiothreitol, 0.5 mM phenylmethanesulfonyl fluoride, 2% (w/v) polyvinylpyrrolidone), and a cell extract was prepared by sonication (two 15 sec. bursts) on ice. The extract was then filtered through fine synthetic mesh (Miracloth, Calbiochem, La Jolla, Calif.) and the pH of the extract filtrate was adjusted to 7.6.

The IAGlu Transferase assay mixture (0.5 mL final volume) 0.8 mM $^{13}C_6$-labeled IAA and 0.024 µCi of 5-[$^3$H]-IAA; 5 mM UDP-glucose; 0.1 mM dithiothreitol; 75 mM 4-(2-hydroxyethyl)-1-piperazine N'-2-ethanesulfonic acid (HEPES) buffer, pH 7.4; 50 mM myo-inositol; and 0.1 ml of cell extract (27 µg protein). Incubation was for 4 hr at 37° C. The reaction was stopped by addition of 0.5 ml of 2-propanol, and protein was removed by centrifugation. The supernatant solution was freed of anionic unesterified IAA by passage through a one ml DEAE-acetate column. The eluate of 50% (v/v) 2-propanol was collected, and the column further washed with the same solvent for a total volume of eluate plus washings of 5.0 ml, as described in Leznicki and Bandurski (1988) Plant Physiol. 88:1474.

The radioactivity in an aliquot of the column eluate was determined by liquid scintillation counting; 44,250 dpm of IAA had been esterified, corresponding to 119 nmoles of putative IAGlu. A small background (1–5%) occurs unless the IAA is freshly purified by (LH-20 Sephadex) chromatography to remove non-ionic radiological decomposition products. The radioactive material eluted from the DEAE-acetate column was pooled and applied to a 10 ml bed volume LH-20 Sephadex column and eluted with 50% (v/v) aqueous ethanol. The material (41,467 dpm) eluting from 7 to 11.2 ml, identical to that for authentic IAGlu (Keglevic, D. (1971) Carbohyd. Res. 20:293) was pooled, and it corresponded to 112 nmoles of IAGlu. This is the expected 10% yield based on the equilibrium of Reaction A in FIG. 1. The pooled material was concentrated to near dryness and applied to a Silica Gel G thin layer chromatography plate and developed with ethyl acetate, methyl ethyl ketone, ethyl alcohol, and water (5:3:1:1) as previously described (Labarca et al. (1965) Biochem. Biophys. Res. Comm 20:641). IAA migrates with an $R_f$ of 0.83, the $R_f$ for authentic IAA-glucose is 0.54. The radioactive material at $R_f$ 0.54 was eluted from the silica gel with one ml of 50% v/v aqueous ethanol and contained 7050 dpm, corresponding to 19 nmoles of IAGlu. The loss of radioactivity is as expected for chromatography of an indolylic compound on Silica Gel. The eluted material was taken to near dryness and analyzed by Fast Atom Bombardment-Mass Spectrometry. Conditions used were a matrix of m-nitrobenzyl alcohol, a cesium ion gun using 2 µA ion flux and 37 kV accelerating voltage. The sample was scanned for compounds in the molecular weight range from 100 to 1200 daltons in a VG-ZAB2S spectrometer (VG Instruments, Ltd., Manchester, England). Authentic unlabeled IAGlu yielded $(M)^+$ of 337.118 and $(M+Na)^+$ of 360.113.

Example 6
Transgenic Tobacco expressing Maize Iaglu Synthetase

Figure 6:
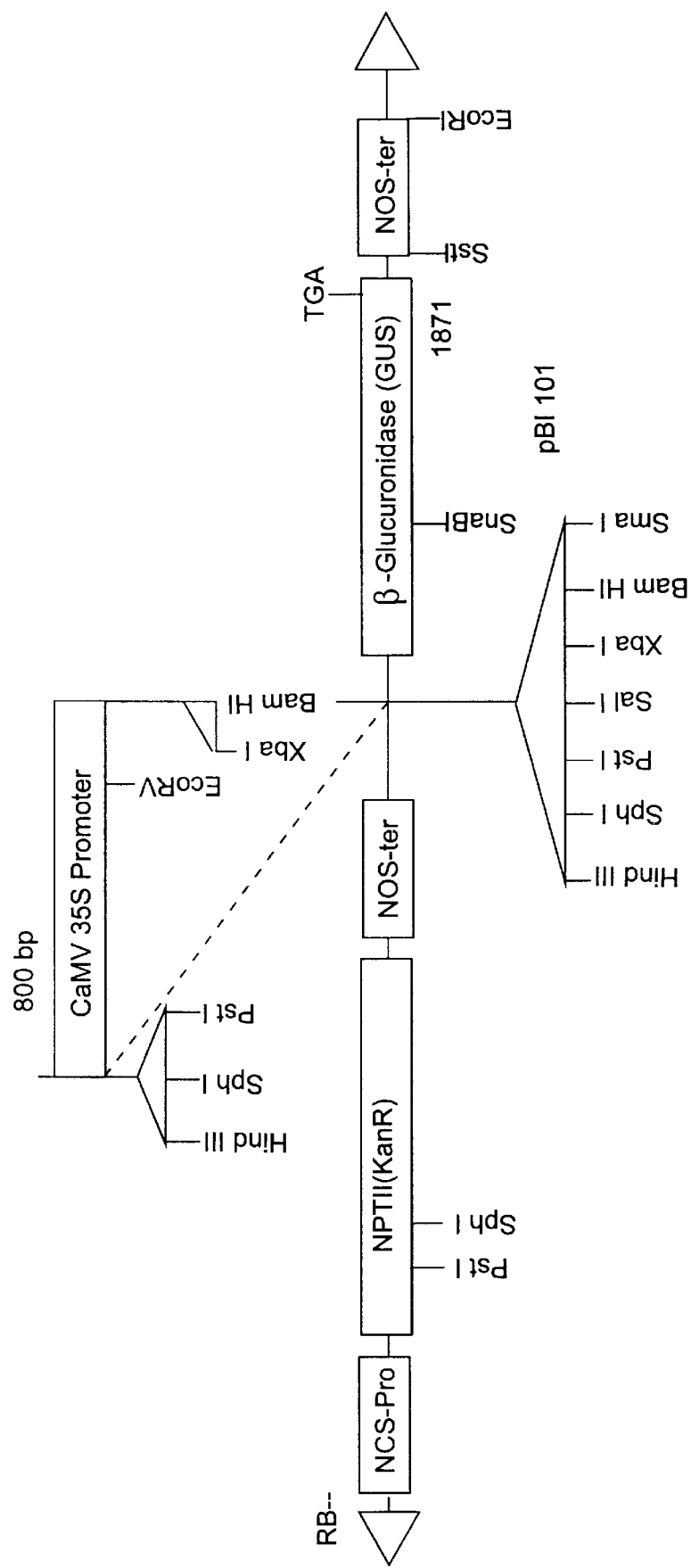
FIG. 6 illustrates the restriction map of a portion of pBI121 with the kanamycin resistance gene, CaMV 35S promoter, polylinker and β-glucuronidase gene.

Recombinant DNA methods were performed according to established methods (Sambrook et al. (1989) supra). The Zea mays iaglu-coding sequence (for IAGlu synthetase) as described herein was isolated from positive clone #3 as a BamHI-EcORV fragment, and it was positioned in the sense orientation downstream of the CaMV 35S RNA promoter of the pBI121 binary vector cut with SstI and made blunt-ended with the Klenow fragment of DNA Polymerase I and then digested with BamHI to yield plasmid $P_{35S}$-iaglu. The pB121 vector is pBI101 into which an approximately 800 bp fragment containing the 35S CaMV promoter has been cloned. pBI121 is commercially available from Clontech (Palo Alto, Calif.). FIG. 6 illustrates the relevant portion of pBI121. The presence of this plasmid and its derivatives is selected by growth on kanamycin. pBI101 is a "promoter-less" GUS cassette in the Agrobacterium binary plasmid vector pBIN19 (Bevan, M. (1984) Nucl. Acids Res. 12:8711). Both the $P_{35}S$-iaglu construct and the control binary vector pBI121 (containing the 35S-gus fusion) were transformed in parallel samples of Agrobacterium tumefaciens strain LBA4404 by electrotransformation. LBA4404 is a well known Agrobacterium tumefaciens strain carrying the transacting virulence functions necessary to facilitate the transfer of the T-DNA region of binary vectors to plants. The strain is resistant to streptomycin and is Thi$^+$, which allows a strong selection for growth on minimal plates after triparental mating, as the E. coli donor strains (typically MC1022, DH5, or HB101) are Thi$^-$ (Hoekema et al. (1983) Nature 303:179).

The Nicotiana tabacum SR-1 plants used for transformation were grown axenically on solid MS media (MS salts (Sigma Chemical Co., St. Louis, Mo.), 30 g/L sucrose, 0.56 mM myo-inositol, buffered to pH 5.7 with 2.5 mM 2-[N-morpholino]ethanesulfonic acid (MES), 0.8% tissue culture grade agar (Phytagar, trademark of GIBCO/BRL, Life Technologies, Inc., Gaithersburg, Md.). Leaves from these plants were transferred to solid medium A (MS salts, 30 g/L sucrose, 1.2 µM thiamine, 0.56 mM myo-inositol, 1 µM indole-3-acetic acid, 10 µM benzylaminopurine (BAP), buffered to pH 5.6 with 2.5 mM MES, 0.8% Phytagar) and infected with Agrobacterium strains containing either $P_{35S}$-iaglu or the pBI121 control binary vector using syringe needles. After 3 days, the leaves were transferred to medium A containing 200 µg/ml kanamycin and 500 µg/ml carbenicillin. Kanamycin selects for the presence of recombinant DNA sequences, and carbenicillin selects against the A. tumefaciens. Emerging shoots were transferred to MS medium (containing 100 µg/ml kanamycin and 500 µg/ml carbenicillin) to induce rooting.

Example 7
IAGlu Transferase Antisense Plasmids and Transgenic Plants

To make a plasmid to express an antisense RNA capable of inhibiting the translational expression of a natural iaglu gene in a plant, cDNA clone #3 is cleaved with EcoRI and the fragment ends are made blunt with the Klenow fragment of DNA polymerase. Plasmid pBI121 is digested with BamHI and SstI, and the ends are made blunt with the Klenow fragment of DNA polymerase. Then, the cDNA fragment and the linearized pBI121 are ligated, and the ligation mixture is transformed into E. coli and transformants are selected by plating on kanamycin-containing agar.

Figure 4A:
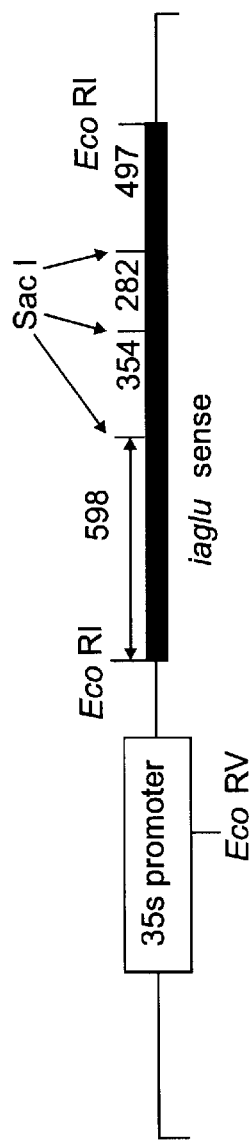
FIGS. 4A–4B illustrates the CaMV 35S promoter region of pBI121 and insertion of the iaglu cDNA in the sense orientation with respect to the 35S promoter. The numbers represent restriction fragment sizes (bp) within the iaglu cDNA portion.
Figure 4B:
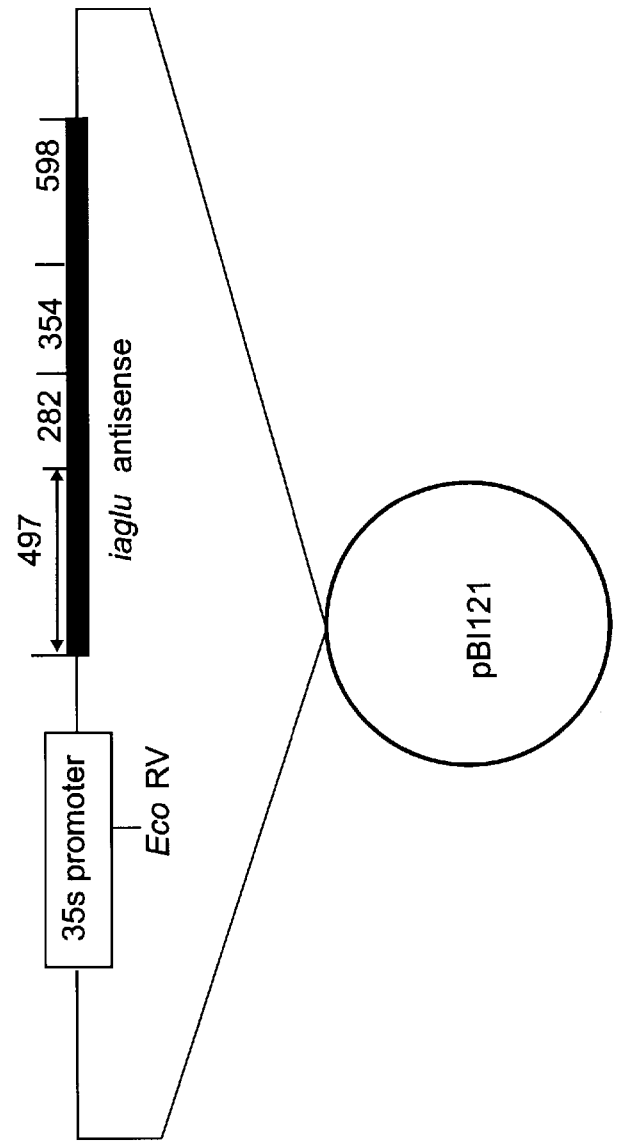

To identify recombinant plasmids in which the iaglu cDNA is inserted in the reverse (antisense) orientation with respect to the CaMV 35S promoter, plasmids are prepared from transformants, digested with EcoRV and SacI, and the resulting fragments are size fractionated by agarose gel electrophoresis, and plasmids having the desired orientation are identified (see scheme presented in FIG. 4). The antisense orientation is characterized as having an EcoRV-SacI fragment of about 100 bp shorter than observed for the sense orientation.

Figure 5:
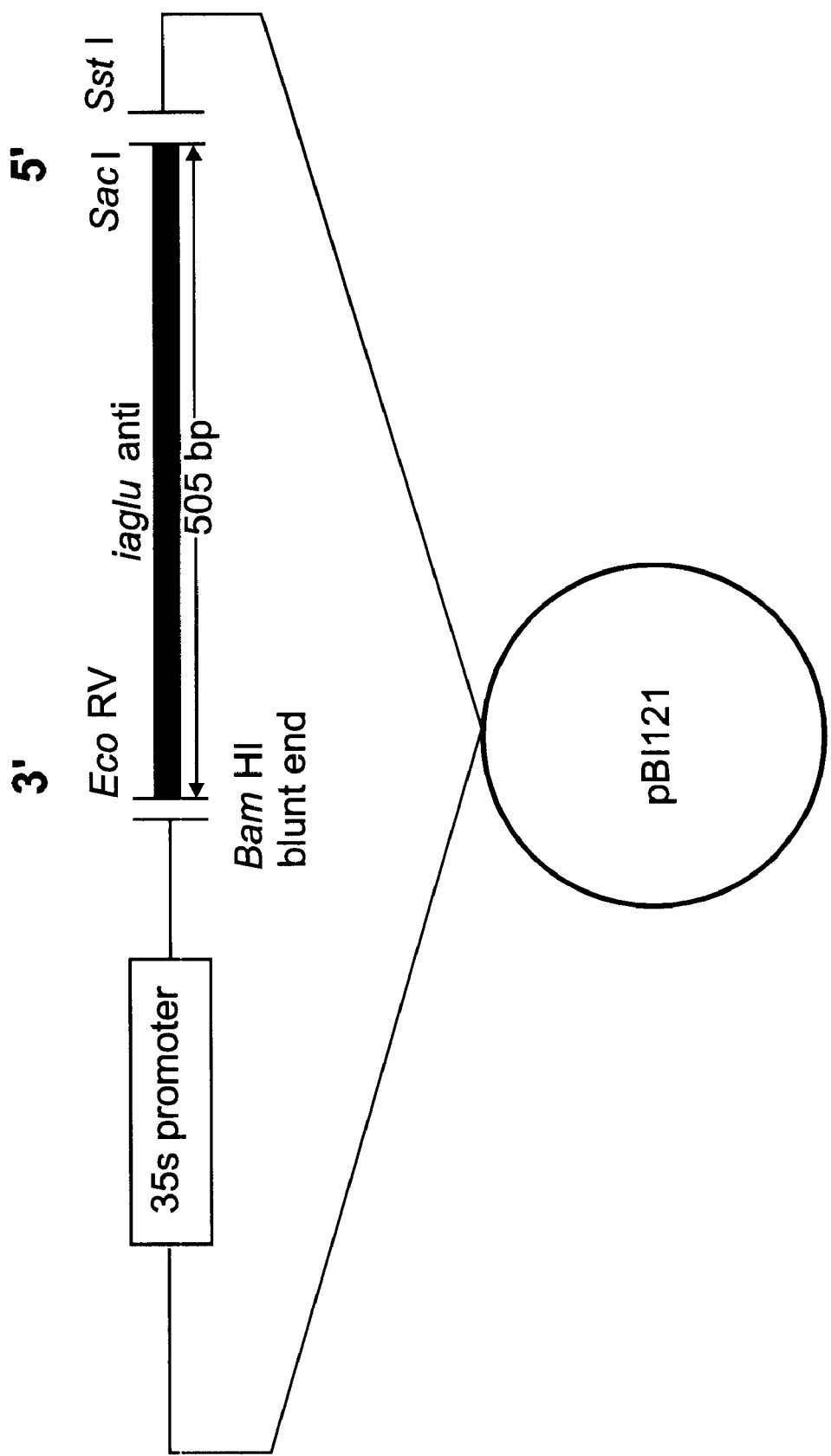
FIG. 5 illustrates pBI121 into which a 505 bp EcoRV-SacI fragment comprising the 3' region of the iaglu cDNA coding sequence has been cloned in the antisense direction. See also Example 7.

To create a plasmid from which antisense RNA is made corresponding to the 3'portion of the coding sequence, cDNA clone #3 is digested with SacI and EcoRV and a 505 bp SacI-EcoRV fragment is inserted into pBI121 which has been digested with BamHI, blunt ended using the fill-in reaction of DNA polymerase Klenow fragment, and then digested with SstI. The fragments are then ligated. The ligation mixture is transformed into suitable E. coli host cells, and transformants are selected by plating on solid nutrient medium containing kanamycin. The plasmid contents of transformants are analyzed by restriction endonuclease digestion to identify one of the desired nature. See FIG. 5 for a diagram of the relevant portion of the desired plasmid.

Other iaglu antisense RNA-expressing plasmids can be constructed as follows: cDNA clone #3 is digested with Sau3A, and a fragment of about 776 bp is isolated and purified after agarose gel electrophoresis of the digested plasmid. This provides an iaglu-derived sequence corresponding to nucleotides 42 to 817 as given in SEQ ID NO:1, and this fragment includes the ribosome binding site of the iaglu transcript, so that when the antisense RNA is synthesized, there will be a sequence synthesized which will be capable of base pairing with the ribosome binding site of the iaglu mRNA. The ends of the Sau3A fragment are made blunt with the Klenow fragment of DNA polymerase. pBI121 is digested with SstI and BamHI, the ends are made blunt with the Klenow enzyme, and the linearized plasmid, called pBI121-DEL due to the deletion of the β-glucuronidase gene, is then gel purified. Then the purified iaglu fragment and the treated plasmid are ligated together, and the ligation mixture is transformed into competent E. coli, with selection for kanamycin resistance. Transformants are analyzed for their plasmid content and insert orientation by cutting with EcoRV and SacI and agarose gel electrophoresis, and at least one is chosen which contains the appropriate iaglu-derived fragment inserted in an antisense orientation relative to the CaMV 35S promoter; this plasmid is designated pBI121-DEL-anti1. The antisense orientation of the Sau3A fragment will give an EcoRV-SacI fragment which is 338 bp longer than when the iaglu Sau3A fragment is inserted into pBI121-DEL in the sense orientation. Alternatively, the ligation mixture can be electrotransformed directly into A. tumefaciens, and the plasmids then characterized to verify the antisense orientation of the iaglu-derived insert relative to the 35S promoter. SacI cuts after nucleotide 598 within SEQ ID NO: 1, which is contained within the 776 bp Sau3A fragment, and EcoRV cuts within the CaMV 35S promoter sequence.

The desired antisense plasmid is then introduced into A. tumefaciens LB4404 by triparental mating with E. coli (pRK2013), and then is transferred into plant tissue as described herein. The transformed plant tissue is subjected to selection for the presence of the plasmid, and then transgenic plants are regenerated from the transformed plant tissue as described herein above.

The desired pBI121-antisense plasmid is then introduced into A. tumefaciens LB4404 by triparental mating with E. coli (pRK2013) (see e.g., Ditta et al. (1980) Proc. Natl. Acad. Sci. USA 77:7347), and then is transferred into plant tissue as described herein. The transformed plant tissue is subjected to selection for the presence of the plasmid, and then transgenic plants are regenerated from the transformed plant tissue as described herein above.

While various embodiments of the present invention have been described in detail, it is apparent that modifications, extensions, adaptations and optimizations may occur to those skilled in the art. It is to be expressly understood that such modifications and adaptations and so on are within the spirit and scope of the present invention, as set forth in the following claims.

We claim:

1. A non-naturally occurring nucleic acid molecule comprising a nucleotide sequence, wherein said nucleotide sequence encodes a UDP-glucose indol-3-ylacetylglucosyl transferase (IAGlu Transferase), said IAglu transferase having an amino acid sequence as given in SEQ ID NO:2.

2. The non-naturally occurring nucleic acid molecule of claim 1 wherein said nucleotide sequence is given in SEQ ID NO:1 from nucleotide 57 through nucleotide 1469.

3. An antisense construct comprising:
   a promoter portion, said promoter being fictional in a plant cell;
   and an iaglu antisense portion, said promoter portion being operably linked to said iaglu antisense portion; and said antisense portion oriented with respect to said promoter portion such that RNA produced is complementary in nucleotide sequence and capable of binding or hybridizing to mRNA encoding UDP-glucose indol-3ylglucosyl transferase, wherein said iaglu antisense portion has a nucleotide sequence as given in at least 15 contiguous nucleotides of SEQ ID NO:1.

4. The antisense construct of claim 3, wherein said iaglu antisense portion has a nucleotide sequence as given in SEQ ID NO:1 from nucleotide 42 to nucleotide 817.

5. The antisense construct of claim 3, wherein said iaglu antisense portion has a nucleotide sequence as given in SEQ ID NO:1 from nucleotide 1234 to nucleotide 1731.

6. The antisense construct of claim 3, wherein said iaglu antisense portion has a nucleotide sequence as given in SEQ ID NO:1.

7. A method for inhibiting IAGlu Transferase gene expression in a plant having a natural IAGlu Transferase gene, said method comprising the steps of
   a) cloning the antisense construct of claim 3 into a vector adapted for use in a plant cell to produce an antisense vector;
   b) introducing the antisense vector of step (a) into a plant tissue to produce transgenic plant tissue;
   c) regenerating a transgenic plant from the transgenic plant tissue of step (b),
whereby said antisense construct is transcribed in at least one tissue of said transgenic plant at a level sufficient to inhibit the expression of the natural IAGlu Transferase gene of said transgenic plant to below natural IAGlu Transferase levels, and whereby the inhibition of said IAGlu transferase gene expression has at least one effect in a plant, said effects selected from the group consisting of enhanced apical dominance, increased cell enlargement, increased stem elongation, increased root growth, increased underground stem growth, decreased branching and improved fruit growth.

8. The method of claim 7 wherein said transgenic plant is a dicotyledonous plant.

9. The method of claim 8 wherein said dicotyledonous plant is a member of the Solanaceae.

10. The method of claim 7 wherein said transgenic plant is a monocotyledonous plant.

11. The method of claim 10 wherein said monocotyledonous plant is selected from the group consisting of maize, rice, barley and wheat.

12. A method for inhibiting IAGlu Transferase gene expression in a plant having a natural IAGlu Transferase gene, said method comprising the steps of
   a) cloning the iaglu antisense construct of claim 3 into a vector adapted for use in a plant cell to produce an antisense vector; wherein said antisense construct comprises a nucleotide sequence of at least 100 bp as given in SEQ ID NO:1;
   b) introducing the antisense vector of step (a) into a plant tissue to produce transgenic plant tissue; and
   c) regenerating a transgenic plant from the transgenic plant tissue of step (b),
whereby said antisense construct is transcribed in at least one tissue of said transgenic plant at a level sufficient to inhibit the expression of the natural IAGlu Transferase gene of said transgenic plant to below natural IAGlu Transferase levels, and whereby the inhibition of said IAGlu Transferase gene expression has at least one effect in a plant, said effects selected from the group consisting of enhanced apical dominance, increased cell enlargement, increased stem elongation, increased root growth, increased underground stem growth, decreased branching and improved fruit growth.

13. The method of claim 12 wherein said antisense construct comprises a nucleotide sequence of at least 100 bp as given in SEQ ID NO:1 between nucleotide 1 and nucleotide 858.

14. A transgenic plant comprising of an iaglu antisense construct comprising; a promoter portion, said promoter being functional in a plant cell; and an iaglu antisense portion, said promoter portion being operably linked to said iaglu antisense portion; and said antisense portion oriented with respect to said promoter portion such that RNA produced is complementary in nucleotide sequence and capable of binding or hybridizing to mRNA encoding IAGlu Transferase, wherein said antisense construct comprises a nucleotide sequence of at least 15 bp as given in SEQ ID NO:1.

15. The transgenic plant of claim 14 wherein antisense construct comprises a nucleotide sequence given in SEQ ID NO:1 from nucleotide 42 to nucleotide 1731.

16. The transgenic plant of claim 14 wherein said antisense construct comprises a nucleotide sequence given in SEQ ID NO:1 from nucleotide 1 to nucleotide 1731.

17. The transgenic plant of claim 14 wherein said transgenic plant is a dicotyledonous plant.

18. The transgenic plant of claim 17 wherein said plant is a member of the Solanaceae.

19. The transgenic plant of claim 14 wherein said plant is a monocotyledonous plant.

20. The transgenic plant of claim 19 wherein said plant is selected from the group consisting of corn, rice, wheat and barley.

21. A method of producing a transgenic plant, said method comprising the steps of:
   a) introducing the iaglu antisense construct of claim 3 into a plant cell to produce a transgenic plant cell;
   b) regenerating a transgenic plant from the transgenic plant cell of step (a); and
   c) growing the transgenic plant under conditions which allow the expression of said iaglu construct,
whereby IAGlu Transferase synthesis is inhibited with the result that said transgenic plant has lower than natural levels of IAGlu Transferase.

* * * * *

UNITED STATES PATENT AND TRADEMARK OFFICE
CERTIFICATE OF CORRECTION

PATENT NO.   : 5,919,998

DATED        : July 6, 1999

INVENTOR(S)  : Bandurski et al.

It is certified that error appears in the above-identified patent and that said Letters Patent is hereby corrected as shown below:

On the Title Page, under [56] Other Publications, under "Van Onckelen", please delete "*131*:373-376."
and replace with --181:373-376.--.
In Column 6, line 61, please delete "*Oryctolaqus*" and replace with --*Oryctolagus*--.
In Column 6, line 65, please delete "rluq23" and replace with --rlug23--.
In Columns 7 and 8, in Table 1, under A., between rows "HlugP4" and "IAGlu", all of the lines after
"| || |:| ||" need to be moved one space to the right.
In Columns 7 and 8, in Table 1, under B., between rows "UGT2B13$^e$" and "IAGlu$^f$" need to be moved
one space to the left.
In Column 7, line 50, please delete "botrytis," and replace with --*botrytis*,--.
In Column 15, line 57, please delete "BamHI-EcORV" and replace with --BamHI-EcoRV--.
In Column 16, line 59, please delete "3'portion" and replace with --3' portion--.
In Column 29, line 54, please delete "fictional" and replace with --functional--.
In Column 32, line 14, please delete "1731." and replace with --817.--.

Signed and Sealed this

First Day of February, 2000

*Attest:*

Q. TODD DICKINSON

*Attesting Officer*     Acting Commissioner of Patents and Trademarks

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 1731 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 57..1472

(xi) SEQUENCE DESCRIPTION: SEQ ID NO:1:

```
GAATTCGTCG GCCGCCACCT AACATCCATT GTTGCAAGAA GGATCAAGGA ACAACC            56

ATG GCG CCG CAT GTC CTC GTC GTG CCC TTC CCC GGT CAG GGA CAC ATG        104
Met Ala Pro His Val Leu Val Val Pro Phe Pro Gly Gln Gly His Met
 1               5                  10                  15

AAC CCC ATG GTA CAG TTC GCC AAG AGG CTG GCA TCC AAG GGC GTG GCC        152
Asn Pro Met Val Gln Phe Ala Lys Arg Leu Ala Ser Lys Gly Val Ala
                20                  25                  30

ACC ACG CTC GTC ACC ACC CGC TTC ATC CAG AGG ACT GCC GAC GTG GAC        200
Thr Thr Leu Val Thr Thr Arg Phe Ile Gln Arg Thr Ala Asp Val Asp
            35                  40                  45

GCG CAC CCA GCG ATG GTC GAG GCC ATC TCC GAC GGG CAC GAC GAG GGA        248
Ala His Pro Ala Met Val Glu Ala Ile Ser Asp Gly His Asp Glu Gly
```

-continued

```
               50                      55                      60
GGG TTC GCG TCG GCC GCG GGC GTT GCC GAG TAC CTG GAG AAG CAG GCG     296
Gly Phe Ala Ser Ala Ala Gly Val Ala Glu Tyr Leu Glu Lys Gln Ala
 65                  70                  75                  80

GCC GCC GCG TCG GCG TCG CTG GCG TCG CTC GTC GAG GCA CGC GCG TCG     344
Ala Ala Ala Ser Ala Ser Leu Ala Ser Leu Val Glu Ala Arg Ala Ser
                 85                  90                  95

TCT GCG GAC GCC TTC ACG TGC GTC GTG TAC GAC TCG TAC GAG GAC TGG     392
Ser Ala Asp Ala Phe Thr Cys Val Val Tyr Asp Ser Tyr Glu Asp Trp
            100                 105                 110

GTG CTG CCC GTG GCG CGG CGA ATG GGC CTG CCC GCC GTC CCC TTC TCC     440
Val Leu Pro Val Ala Arg Arg Met Gly Leu Pro Ala Val Pro Phe Ser
        115                 120                 125

ACG CAG TCG TGC GCC GTC AGC GCC GTG TAC TAC CAC TTC AGC CAG GGG     488
Thr Gln Ser Cys Ala Val Ser Ala Val Tyr Tyr His Phe Ser Gln Gly
    130                 135                 140

AGG CTT GCC GTG CCT CCG GGG GCG GCC GCG GAC GGC AGC GAC GGT GGT     536
Arg Leu Ala Val Pro Pro Gly Ala Ala Ala Asp Gly Ser Asp Gly Gly
145                 150                 155                 160

GCT GGT GCC GCC GCC CTG AGC GAG GCG TTC CTG GGG CTG CCG GAG ATG     584
Ala Gly Ala Ala Ala Leu Ser Glu Ala Phe Leu Gly Leu Pro Glu Met
                165                 170                 175

GAG AGG TCG GAG CTC CCG TCG TTC GTG TTC GAC CAT GGT CCG TAC CCG     632
Glu Arg Ser Glu Leu Pro Ser Phe Val Phe Asp His Gly Pro Tyr Pro
            180                 185                 190

ACC ATC GCC ATG CAA GCG ATT AAA CAG TTC GCT CAT GCG GGA AAG GAT     680
Thr Ile Ala Met Gln Ala Ile Lys Gln Phe Ala His Ala Gly Lys Asp
        195                 200                 205

GAC TGG GTG CTG TTC AAC TCG TTC GAA GAA CTG GAA ACC GAG GTT TTG     728
Asp Trp Val Leu Phe Asn Ser Phe Glu Glu Leu Glu Thr Glu Val Leu
    210                 215                 220

GCT GGC CTG ACA AAG TAC CTG AAG GCC CGA GCC ATC GGC CCA TGC GTG     776
Ala Gly Leu Thr Lys Tyr Leu Lys Ala Arg Ala Ile Gly Pro Cys Val
225                 230                 235                 240

CCG CTG CCC ACC GCT GGA AGG ACC GCC GGC GCC AAT GGC CGG ATC ACC     824
Pro Leu Pro Thr Ala Gly Arg Thr Ala Gly Ala Asn Gly Arg Ile Thr
                245                 250                 255

TAC GGG GCC AAC CTG GTG AAG CCG GAG GAT GCG TGC ACC AAG TGG CTA     872
Tyr Gly Ala Asn Leu Val Lys Pro Glu Asp Ala Cys Thr Lys Trp Leu
            260                 265                 270

GAC ACC AAG CCC GAC CGC TCC GTG GCC TAC GTC TCC TTC GGC AGC CTC     920
Asp Thr Lys Pro Asp Arg Ser Val Ala Tyr Val Ser Phe Gly Ser Leu
        275                 280                 285

GCG TCC CTG GGC AAC GCC CAG AAG GAG GAG CTC GCG CGC GGC CTC CTC     968
Ala Ser Leu Gly Asn Ala Gln Lys Glu Glu Leu Ala Arg Gly Leu Leu
    290                 295                 300

GCC GCC GGC AAG CCG TTC CTG TGG GTG GTG AGG GCC AGC GAC GAG CAC    1016
Ala Ala Gly Lys Pro Phe Leu Trp Val Val Arg Ala Ser Asp Glu His
305                 310                 315                 320

CAG GTC CCG CGC TAT CTC CTG GCC GAG GCG ACG GCG ACG GGC GCC GCG    1064
Gln Val Pro Arg Tyr Leu Leu Ala Glu Ala Thr Ala Thr Gly Ala Ala
                325                 330                 335

ATG GTC GTG CCC TGG TGC CCG CAG CTG GAC GTG CTG GCG CAC CCG GCC    1112
Met Val Val Pro Trp Cys Pro Gln Leu Asp Val Leu Ala His Pro Ala
            340                 345                 350

GTG GGC TGC TTC GTC ACC CAC TGC GGT TGG AAC TCC ACG CTG GAG GCG    1160
Val Gly Cys Phe Val Thr His Cys Gly Trp Asn Ser Thr Leu Glu Ala
        355                 360                 365

CTC AGC TTC GGC GTG CCT ATG GTG GCG ATG GCG CTG TGG ACG GAC CAG    1208
Leu Ser Phe Gly Val Pro Met Val Ala Met Ala Leu Trp Thr Asp Gln
```

```
              370                 375                 380
CCG ACC AAC GCT CGG AAC GTC GAG CTC GCC TGG GGC GCG GGC GTG CGC    1256
Pro Thr Asn Ala Arg Asn Val Glu Leu Ala Trp Gly Ala Gly Val Arg
385                 390                 395                 400

GCG CGC CGC GAT GCT GGC GCG GGC GTG TTC CTT CGC GGG GAA GTG GAG    1304
Ala Arg Arg Asp Ala Gly Ala Gly Val Phe Leu Arg Gly Glu Val Glu
                405                 410                 415

CGG TGC GTG CGC GCC GTC ATG GAC GGG GGC GAG GCG GCG TCT GCT GCA    1352
Arg Cys Val Arg Ala Val Met Asp Gly Gly Glu Ala Ala Ser Ala Ala
                420                 425                 430

CGC AAG GCG GCG GGG GAA TGG AGG GAC AGG GCT CGC GCC GCG GTG GCA    1400
Arg Lys Ala Ala Gly Glu Trp Arg Asp Arg Ala Arg Ala Ala Val Ala
            435                 440                 445

CCC GGT GGC AGC TCT GAC CGC AAC CTG GAC GAG TTC GTG CAG TTT GTG    1448
Pro Gly Gly Ser Ser Asp Arg Asn Leu Asp Glu Phe Val Gln Phe Val
        450                 455                 460

CGC GCC GGC GCC ACG GAG AAG TGA GAGGCGCTGG CTGTGAAGTG TGAAGGGAGG    1502
Arg Ala Gly Ala Thr Glu Lys  *
465                 470

TGATGTTGCA GGGTCCCAGA TGTGACGACG CGATGCGAAG GAGAAACGTT TCGAAACTGG    1562

AAGCAAAAAA CGGTCGAAAG TTGGTGCCTC TACTTGGTTT GGTTTATGCT TTGGGTCCAC    1622

CAGCCATAAT AATATACTTT GCTTGAGGAT TCTACCATAA CAATTATTCA GCCTTTTATT    1682

TTCTACCCTA TGAAAAAGA AAGGTATGTT GTGCCATGCA GGGTTAAAA                 1731

(2) INFORMATION FOR SEQ ID NO:2:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Pro His Val Leu Val Pro Phe Pro Gly Gln Gly His Met
1               5                   10                  15

Asn Pro Met Val Gln Phe Ala Lys Arg Leu Ala Ser Lys Gly Val Ala
                20                  25                  30

Thr Thr Leu Val Thr Thr Arg Phe Ile Gln Arg Thr Ala Asp Val Asp
            35                  40                  45

Ala His Pro Ala Met Val Glu Ala Ile Ser Asp Gly His Asp Glu Gly
        50                  55                  60

Gly Phe Ala Ser Ala Ala Gly Val Ala Glu Tyr Leu Glu Lys Gln Ala
65              70                  75                  80

Ala Ala Ala Ser Ala Ser Leu Ala Ser Leu Val Glu Ala Arg Ala Ser
                85                  90                  95

Ser Ala Asp Ala Phe Thr Cys Val Val Tyr Asp Ser Tyr Glu Asp Trp
            100                 105                 110

Val Leu Pro Val Ala Arg Arg Met Gly Leu Pro Ala Val Pro Phe Ser
        115                 120                 125

Thr Gln Ser Cys Ala Val Ser Ala Val Tyr Tyr His Phe Ser Gln Gly
    130                 135                 140

Arg Leu Ala Val Pro Pro Gly Ala Ala Ala Asp Gly Ser Asp Gly Gly
145                 150                 155                 160

Ala Gly Ala Ala Ala Leu Ser Glu Ala Phe Leu Gly Leu Pro Glu Met
                165                 170                 175

Glu Arg Ser Glu Leu Pro Ser Phe Val Phe Asp His Gly Pro Tyr Pro
```

```
                      180                 185                 190
Thr Ile Ala Met Gln Ala Ile Lys Gln Phe Ala His Ala Gly Lys Asp
                195                 200                 205
Asp Trp Val Leu Phe Asn Ser Phe Glu Leu Glu Thr Glu Val Leu
210                 215                 220
Ala Gly Leu Thr Lys Tyr Leu Lys Ala Arg Ala Ile Gly Pro Cys Val
225                 230                 235                 240
Pro Leu Pro Thr Ala Gly Arg Thr Ala Gly Ala Asn Gly Arg Ile Thr
                245                 250                 255
Tyr Gly Ala Asn Leu Val Lys Pro Glu Asp Ala Cys Thr Lys Trp Leu
                260                 265                 270
Asp Thr Lys Pro Asp Arg Ser Val Ala Tyr Val Ser Phe Gly Ser Leu
                275                 280                 285
Ala Ser Leu Gly Asn Ala Gln Lys Glu Glu Leu Ala Arg Gly Leu Leu
                290                 295                 300
Ala Ala Gly Lys Pro Phe Leu Trp Val Val Arg Ala Ser Asp Glu His
305                 310                 315                 320
Gln Val Pro Arg Tyr Leu Leu Ala Glu Ala Thr Ala Thr Gly Ala Ala
                325                 330                 335
Met Val Val Pro Trp Cys Pro Gln Leu Asp Val Leu Ala His Pro Ala
                340                 345                 350
Val Gly Cys Phe Val Thr His Cys Gly Trp Asn Ser Thr Leu Glu Ala
                355                 360                 365
Leu Ser Phe Gly Val Pro Met Val Ala Met Ala Leu Trp Thr Asp Gln
                370                 375                 380
Pro Thr Asn Ala Arg Asn Val Glu Leu Ala Trp Gly Ala Gly Val Arg
385                 390                 395                 400
Ala Arg Arg Asp Ala Gly Ala Gly Val Phe Leu Arg Gly Glu Val Glu
                405                 410                 415
Arg Cys Val Arg Ala Val Met Asp Gly Gly Glu Ala Ala Ser Ala Ala
                420                 425                 430
Arg Lys Ala Ala Gly Glu Trp Arg Asp Arg Ala Arg Ala Ala Val Ala
                435                 440                 445
Pro Gly Gly Ser Ser Asp Arg Asn Leu Asp Glu Phe Val Gln Phe Val
450                 455                 460
Arg Ala Gly Ala Thr Glu Lys
465                 470

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: N-terminal (ix) FEATURE:
        (A) NAME/KEY: Protein
        (B) LOCATION: 1..12
        (D) OTHER INFORMATION: /note= "Xs = amino acids which
            could not be identified with certainty."

(xi) SEQUENCE DESCRIPTION: SEQ ID NO:3:

Met Ala Pro Xaa Val Leu Val Val Pro Phe Pro Gly Gln Gly Xaa Met
```

```
                    1               5                   10
Asn Pro
    15

(2) INFORMATION FOR SEQ ID NO:4:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:4:

Ile Leu Val Lys Trp Leu Pro Gln Asn Asp Leu Leu Gly His Pro Met
1               5                   10                  15

Thr Arg Ala Phe Ile Thr His Ala Gly Ser His Gly Val Tyr Glu Ser
            20                  25                  30

Ile Cys Asn Gly Val Pro Met Val Met Pro Leu Phe Gly Asp Gln
        35                  40                  45

Met Asp Asn Ala Lys Arg Met Glu
    50                  55

(2) INFORMATION FOR SEQ ID NO:5:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:5:

Cys Thr Lys Trp Leu Asp Thr Lys Pro Asp Arg Ser Val Ala Tyr Val
1               5                   10                  15

Ser Phe Gly Ser Leu Ala Ser Leu Gly Asn Ala Gln Lys Glu Glu Leu
            20                  25                  30

Ala Arg Gly Leu Leu Ala Ala Gly Lys Pro Phe Leu Trp Val Val Arg
            35                  40                  45

Ala Ser Asp Glu His Gln Val Pro Arg Tyr Leu Leu Ala Glu Ala Thr
    50                  55                  60

Ala Thr Gly Ala Ala Met Val Val Pro Trp Cys Pro Gln Leu Asp Val
65                  70                  75                  80

Leu Ala His Pro Ala Val Gly Cys Phe Val Thr His Cys Gly Trp Asn
                85                  90                  95

Ser Thr Leu Glu Ala Leu Ser Phe Gly Val Pro Met Val Ala Met Ala
            100                 105                 110

Leu Trp Thr Asp Gln Pro Thr Asn Ala Arg Asn Val Glu Leu Ala Trp
            115                 120                 125

Gly Ala Gly
    130

(2) INFORMATION FOR SEQ ID NO:6:
```

(i) SEQUENCE CHARACTERISTICS:
    (A) LENGTH: 131 amino acids
    (B) TYPE: amino acid
    (C) STRANDEDNESS: single
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:6:

```
Cys Leu Ala Trp Leu Gly Arg Gln Pro Ala Arg Gly Val Ala Tyr Val
1               5                   10                  15

Ser Phe Gly Thr Val Ala Cys Pro Arg Pro Asp Glu Leu Arg Glu Leu
            20                  25                  30

Ala Ala Gly Leu Glu Asp Ser Gly Ala Pro Phe Leu Trp Ser Leu Arg
            35                  40                  45

Glu Asp Ser Trp Pro His Leu Pro Pro Gly Phe Leu Asp Arg Ala Ala
        50                  55                  60

Gly Thr Gly Ser Gly Leu Val Val Pro Trp Ala Pro Gln Val Ala Val
65                  70                  75                  80

Leu Arg His Pro Ser Val Gly Ala Phe Val Thr His Ala Gly Trp Ala
                85                  90                  95

Ser Val Leu Glu Gly Leu Ser Ser Gly Val Pro Met Ala Cys Arg Pro
            100                 105                 110

Phe Phe Gly Asp Gln Arg Met Asn Ala Arg Ser Val Ala His Val Trp
            115                 120                 125

Gly Phe Gly
    130
```

(2) INFORMATION FOR SEQ ID NO:7:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:7:

```
Trp Ile Pro Gln Asn Asp Leu Leu Gly His Pro Lys Thr Arg Ala Phe
1               5                   10                  15

Ile Thr His Gly Gly Thr Asn Gly Leu Tyr Glu Ala Ile Tyr His Gly
            20                  25                  30

Val Pro Met Val Gly Ile Pro Leu Phe Gly Asp Gln Pro Asp Asn Ile
            35                  40                  45

Ala Arg Val Lys
    50
```

(2) INFORMATION FOR SEQ ID NO:8:

(i) SEQUENCE CHARACTERISTICS:
        (A) LENGTH: 63 amino acids
        (B) TYPE: amino acid
        (C) STRANDEDNESS: single
        (D) TOPOLOGY: linear -continued (ii) MOLECULE TYPE: protein (iii) HYPOTHETICAL: NO (v) FRAGMENT TYPE: internal (xi) SEQUENCE DESCRIPTION: SEQ ID NO:8:

Ala Thr Ala Thr Gly Ala Ala Met Val Val Pro Trp Cys Pro Gln Leu
1               5                   10                  15

Asp Val Leu Ala His Pro Ala Val Gly Cys Phe Val Thr His Cys Gly
                20                  25                  30

Trp Asn Ser Thr Leu Glu Ala Leu Ser Phe Gly Val Pro Met Val Ala
            35                  40                  45

Met Ala Leu Trp Thr Asp Gln Pro Thr Asn Ala Arg Asn Val Glu
    50                  55                  60

(2) INFORMATION FOR SEQ ID NO:9:

(i) SEQUENCE CHARACTERISTICS:
            (A) LENGTH: 58 amino acids
            (B) TYPE: amino acid
            (C) STRANDEDNESS: single
            (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:9:

Ala Thr Leu Gly Pro Ile Thr Arg Val Tyr Lys Trp Leu Pro Gln Asn
1               5                   10                  15

Asp Ile Leu Gly His Pro Lys Thr Lys Ala Phe Val Thr His Gly Gly
                20                  25                  30

Ala Asn Gly Leu Tyr Glu Ala Ile Tyr His Gly Ile Pro Met Ile Gly
            35                  40                  45

Ile Pro Leu Phe Gly Asp Gln Pro Asp Asn
    50                  55